United States Patent [19]

Hamill et al.

[11] Patent Number: 4,659,660

[45] Date of Patent: Apr. 21, 1987

[54] A47934 ANTIBIOTIC AND PROCESS FOR PRODUCTION THEREOF

[75] Inventors: Robert L. Hamill, Greenwood; Ralph E. Kastner, Indianapolis, both of Ind.

[73] Assignee: Eli Lilly and Company, Indianapolis, Ind.

[21] Appl. No.: 740,926

[22] Filed: Jun. 3, 1985

Related U.S. Application Data

[62] Division of Ser. No. 607,864, Jun. 22, 1984, Pat. No. 4,537,879, which is a division of Ser. No. 403,842, Jul. 30, 1982, Pat. No. 4,462,942.

[51] Int. Cl.[4] .................... C12P 21/04; C12P 17/18; C12N 1/20; C12R 1/465
[52] U.S. Cl. ........................ 435/71; 435/70; 435/253; 435/886; 435/119
[58] Field of Search ............ 435/70, 71, 119, 253, 435/886, 68

[56] References Cited

U.S. PATENT DOCUMENTS 4,169,140 9/1979 Ohba et al. ...................... 424/117

OTHER PUBLICATIONS

Chem. Abs., vol. 90, p. 470, #202214s, *Antitick Reagent, Gouguillotine,* Hagihara et al., 1979.

*Primary Examiner*—Charles F. Warren
*Assistant Examiner*—John Edward Tarcza
*Attorney, Agent, or Firm*—Paul C. Steinhardt

[57] ABSTRACT

Antibiotic A47934 is produced by submerged, aerobic fermentation of new *Streptomyces toyocaensis* NRRL 15009. The antibiotic is active against gram-positive bacteria in vitro and in vivo. It promotes growth in poultry and swine and serves to enhance feed efficiency in ruminant animals having a developed rumen.

5 Claims, 1 Drawing Figure

A47934 ANTIBIOTIC AND PROCESS FOR PRODUCTION THEREOF

This application is a division of application Ser. No. 607,864, filed June 22, 1984, now U.S. Pat. No. 4,537,879, issued Aug. 27, 1985 which is a divisional of application Ser. No. 403,842, filed July 30, 1982, now U.S. Pat. No. 4,462,942.

BACKGROUND OF THE INVENTION

Many microorganisms are pathogenic and are causative agents in producing diseased states in man and animals.

A large number of antibiotics have been developed, some of which are active against one or more pathogenic microorganisms. However, there remains a need to find agents which are more effective in order to treat the diseases caused by these organisms in man or animals.

The A47934 antibiotic, belonging to the glycopeptide family of antibiotics, is a gram positive antimicrobial agent. Antibiotic A47934 is the sulfate ester of antibiotic A41030 factor A, which is disclosed and claimed by Kastner et al., U.S. application Ser. No. 361,301, filed Mar. 24, 1982.

Glycopeptide antibiotics already known in the art include, inter alia, vancomycin, McCormick et al., U.S. Pat. No. 3,067,099 (Dec. 4, 1962), the structure of vancomycin being reported by Williamson et al., J. Am. Chem. Soc. 103, 6580–6585 (1981); actaplanin (antibiotic A-4696), Hamill et al., U.S. Pat. No. 3,952,095 (Apr. 20, 1976), a portion of the structure of actaplanin being reported by Debono, U.S. Pat. No. No. 4,322,343 (Mar. 30, 1982); ristocetin, British Pat. No. 765,886 (1957), the structure of ristocetin A, one factor of the ristocetin complex, being reported by Kalman et al., J. Am. Chem. Soc. 102, 897–905 (1980); and avoparcin, Kunstmann et al., U.S. Pat. No. 3,338,786 (August 29, 1967), the structure of avoparcin being described by Ellestad et al., J. Am. Chem. Soc. 103, 6522–6524 (1981).

SUMMARY OF THE INVENTION

This invention relates to antibiotic substance A47934 and to the process for its production.

The A47934 antibiotic is produced by culturing *Streptomyces toyocaensis* NRRL 15009, or an A47934-producing mutant or variant thereof, under submerged aerobic fermentation conditions.

Antibiotic A47934 inhibits the growth of gram-positive microorganisms.

DESCRIPTION OF THE DRAWINGS

The infrared absorption spectrum of antibiotic A47934 is presented in the accompanying drawing, as follows.

DETAILED DESCRIPTION OF THE INVENTION

Figure 1:
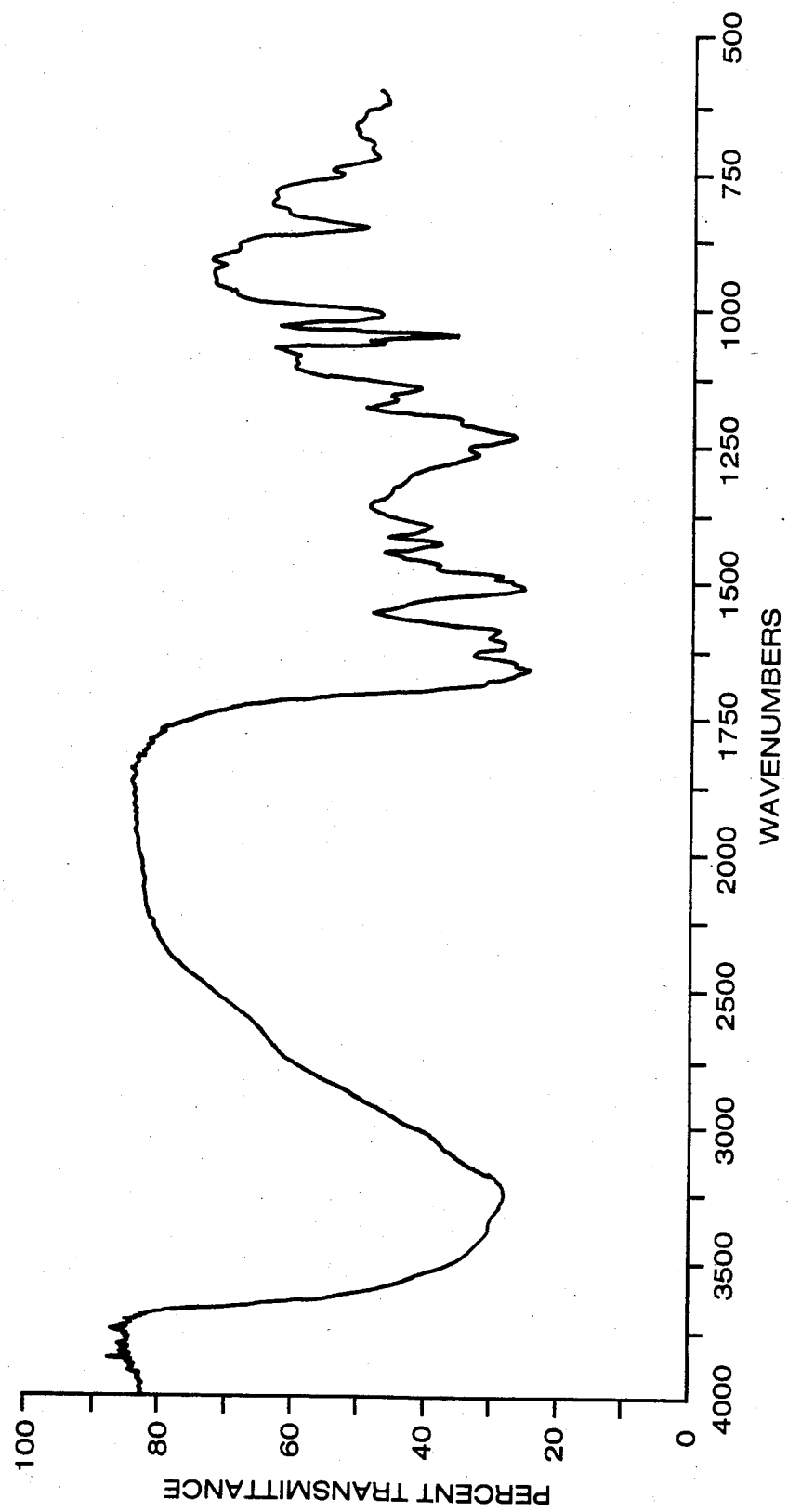
FIG. 1 - A47934 (in KBr pellet)

This invention relates to a novel antibiotic substance having the following formula

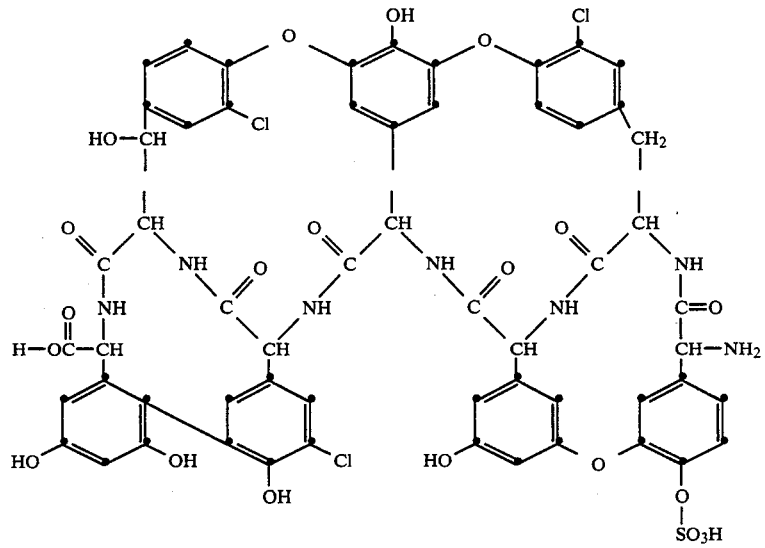

to its preparation, and to the pharmaceutically-acceptable, non-toxic salts of the antibiotic.

Antibiotic A47934 is a white, crystalline compound, having a melting point of >225° C. (dec.). The antibiotic has a molecular weight of about 1311, as determined by fast-atom-bombardment mass spectrometry.

The proton nuclear magnetic resonance spectrum of antibiotic A47934 was determined in dimethylsulfoxide at room temperature. The several six-membered rings of the structural formula are identified by letters of the alphabet, as indicated in the following formula:

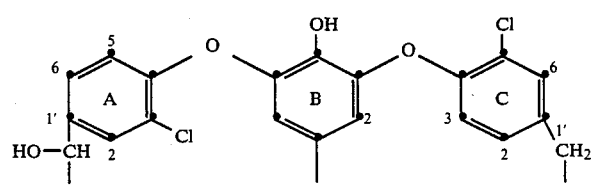

-continued

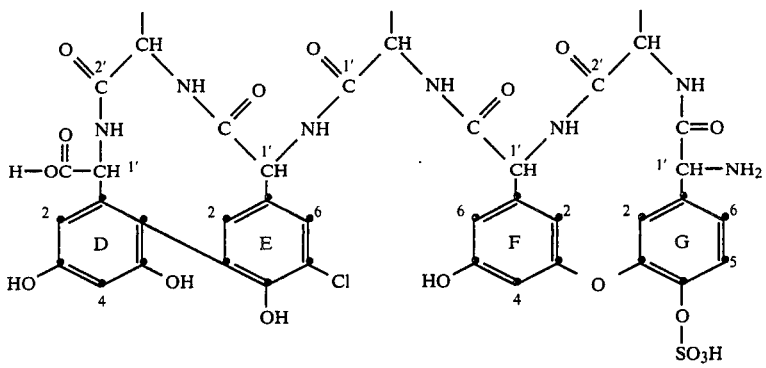

The table of Chemical Shifts follows.

TABLE 1

| Chemical shifts* Assignment | Chem. Shift |
|---|---|
| Ring A | |
| -NH | 6.78 |
| -2' | 4.12 |
| -1' | 5.02 |
| -2 | 7.63 |
| -5 | 7.19 |
| Ring B | |
| -NH | 7.62 |
| -1' | 5.57 |
| -2 | 5.67 |
| -6 | 5.03 |
| Ring C | |
| -NH | 7.45 |
| -2' | 4.86 |
| -1' | 3.30 |
| -2 | 2.82 |
| -3 | 7.16 |
| -6 | 7.20 |
| Ring D | |
| -NH | 8.29 |
| -1' | 4.43 |
| -2 | 6.26 |
| -4 | 6.37 |
| Ring E | |
| -NH | 8.64 |
| -1 | 4.55 |
| -2 | 7.24 |
| -4 | 6.78 |
| Ring F | |
| -NH | 7.65 |
| -1' | 5.21 |
| -2 | 6.38 |
| -4 | 6.35 |
| -6 | 6.30 |
| Ring G | |
| -1' | 4.76 |
| -2 | 6.57 |
| -5 | 7.65 |
| -6 | 7.12 |

*Exchangeable protons are not listed.

Based on the molecular weight and upon the proton nuclear magnetic resonance spectrum data, an empirical formula of $C_{58}H_{44}Cl_3N_7O_{21}S$ is assigned to antibiotic A47934.

Potentiometric titration of the novel antibiotic in 66 percent dimethylformamide in water indicated three titratable groups with $pK_a$ values of about 5.85, 7.9, and 10.3 (initial pH 6.44). However, because the titrimeter does not register below pH 4.0, we were unable to determine the $pK_a$ value for the $-SO_3H$ group. The titration results indicate the A47934 antibiotic is readily able to form salts with bases. The antibiotic will also form salts with strong acids having a pH of 3 or less.

Antibiotic A47934 has specific rotation of $[\alpha]_D^{25°} -1.99$ ($H_2O$, C=10 μg./ml.).

The infrared absorption spectrum of antibiotic A47934 in KBr pellet is shown in the accompanying drawing as FIG. 1. The following distinguishable absorption maxima are observed: 3700–2700 (very broad, intense), 1658 (strong), 1615 (medium), 1590 (medium), 1510 (strong), 1491 (medium), 1472 (weak), 1429 (medium), 1398 (medium), 1326 (very weak), 1265 (medium), 1231 (strong), 1205 (weak), 1163 (weak), 1140 (medium), 1058 (weak), 1045 (medium), 1005 (medium), 849 (medium), 754 (weak), and 719 (weak) $cm^{-1}$.

The ultraviolet absorption spectra of antibiotic A47934 in both acid and neutral water solutions exhibit absorption maxima at 281 nm (ε, 10,850). The ultraviolet absorption spectrum of antibiotic A47934 in basic water solution shows an absorption maximum at 297 nm (ε, 18,900).

The structure of antibiotic A47934 is further confirmed by hydrolysis to yield the antibiotic previously identified as antibiotic A41030 factor A. This latter antibiotic is disclosed and claimed by Kastner et al., in U.S. application Ser. No. 361,301, filed Mar. 24, 1982.

The A47934 antibiotic substance is produced by culturing a hitherto undescribed strain of *Streptomyces toyocaensis* NRRL 15009.

This invention further relates to the biologically pure culture of the hitherto undescribed strain of *Streptomyces toyocaensis* NRRL 15009. For convenience, this culture has been identified in our laboratory as culture A47934.1.

Culture A47934.1 is a variant strain derived through natural selection from culture A47934 which was initially isolated from a low tide sand sample collected from Clayton Bay, Wash.

The antibiotic substance of this invention is arbitrarily designated herein as the A47934 antibiotic.

Culture A47934.1 is classified as a strain of *Streptomyces toyocaensis* based on a comparison with a published description of *Streptomyces griseoflavus* ATCC 25456, by Shirling and Gottlieb, "Cooperative Description of Type Cultures of Streptomyces", *Int. J. Syst. Bacteriol.* 19(4), 391–512 (1969); and with a published description of *Streptomyces toyocaensis* Nishimura, Katagiri, Sato, Mayama and Shimaoka, ATCC 19814, by Shirling and Gottlieb, "Cooperative Description of Type Cultures of Streptomyces", *Int. J. Syst. Bacteriol.* 18(2), 174 (1968), along with certain supplementary tests.

Culture A47934.1 has a spore mass color in the gray (GY) color series, which is different from the yellowish-gray spore mass color of *S. griseoflavus*, as described by Waksman, "The Actinomycetes Vol. II, page 222" [The Williams and Wilkins Co., Baltimore (1961)]. A further difference is that whereas *S. griseoflavus* utilizes mannitol and rhamnose, Culture A47934.1 does not.

Culture A47934.1 is similar culturally, morphologically, and physiologically to *S. toyocaensis* Nishimura, Katagisi, Sato, Mayama and Shimaoka ATCC 19814.

CHARACTERIZATION OF A47934.1 CULTURE

Morphology

Strain A47934.1 produces well-developed, non-fragmenting aerial mycelia which are monopodially branched. Sporophores are arranged in open, short, loose spirals of 2 to 3 coils, and strain A47934.1 is therefore placed in the Spirales (S) section of Pridham et al., "A Guide for the Classification of Streptomycetes According to Selected Groups", *Appl. Microbiol.* 6, 52–79 (1957).

This morphology is best observed on ISP media Nos. 3 and 4. Mature spore chains generally contain from 10 to 50 spores per chain. The spore shape is oblong to oval and the spore surface is spiny. The spore size ranges from 0.58 to 0.71 $\mu M$ in width and from 0.75 to 0.88 $\mu M$ in length, with the average size being 0.65 $\mu M$ wide and 0.83 $\mu M$ long.

Cultural Characteristics

The growth characteristics of Culture A47934.1 on various media are presented in the following Table 1.

Color names were assigned according to the ISCC-NBS Centroid Color Charts Sample No. 2106 (National Bureau of Standards, U.S. Department of Commerce, 1958), and the Color Harmony Manual, 4th Edition (Color Standards Department, Container Corporation of America, Chicago, Ill., 1958).

TABLE 1

| Cultural Characteristics on Various Media | | |
|---|---|---|
| Medium | | Characteristics |
| Yeast extract-malt extract agar (ISP medium #2) | G | Abundant |
| | R | 68.S.OY |
| | Am | Good: 2ih Light Olive Gray |
| | Sp | None |
| Oatmeal agar (ISP medium #3) | G | Good |
| | R | 91.d.gy.Y |
| | Am | Good: 2ih Light Olive Gray |
| | Sp | None |
| Inorganic salts-starch agar (ISP medium #4) | G | Abundant |
| | R | 94.1.01Br |
| | Am | Abundant: 2ih Light Olive Gray |
| | Sp | None |
| Glycerol asparagine agar (ISP medium #5) | G | Abundant |
| | R | 67.brill.OY |
| | Am | Good: 2ih Light Olive Gray |
| | Sp | None |
| Czapek's agar | G | Good |
| | R | 91.d.gy.Y |
| | Am | Good: 2ih Light Olive Gray |
| | Sp | None |
| Tomato paste oatmeal agar | G | Abundant |
| | R | 94.1.01Br |
| | Am | Abundant: 2ih Light Olive Gray |
| | Sp | None |

G = growth
R = reverse
Am = aerial mycelia
Sp = soluble pigment

A comparison of the carbon utilization patterns of Culture A47934.1 and *Streptomyces toyocaensis* ATCC 19814 was conducted using ISP No. 9 basal medium to which filter-sterilized carbon sources were added to equal a final concentration of 1.0%. Plates were read after fourteen days incubation at 30° C. The results are set forth in Table 2, which follows:

TABLE 2

| CARBON UTILIZATION PATTERNS OF A47934.1 AND *S. TOYOCAENSIS* ATCC 19814 | | |
|---|---|---|
| Carbon Source | A47934.1 | ATCC 19814 |
| No carbon | − | − |
| D-Glucose | + | + |
| L-Arabinose | + | + |
| Cellobiose | + | ND |
| D-Fructose | + | + |
| D-Galactose | + | ND |
| i-Inositol | + | + |
| D-Mannitol | − | + |
| Melibiose | − | ND |
| Raffinose | − | − |
| D-Rhamnose | − | − |
| Ribose | + | ND |
| Salicin | − | ND |
| Sucrose | − | − |
| D-Xylose | + | ± |

− = no utilization
+ = utilization
± = doubtful utilization
ND = not done

Cell Wall Studies

Using hydrolyzed whole cells of the organism, the presence of certain diagnostic sugars was determined. The cell-wall sugars were determined using a modification of the procedure of M. P. Lechavalier ["Chemical Methods as Criteria for the Separation of Actinomycetes Into Genera." These methods were developed at workshops sponsored by the Subcommittee on Actinomycetes of the American Society of Microbiology, (Dr. Thomas G. Pridham, Convenor), and held at the Institute of Microbiology, Rutgers University, The State University of New Jersey, New Brunswick, N.J., (1971)].

Hydrolyzed whole cell walls were used to determine the isomers of diaminopimelic acid. The isomers of diaminopimelic acid were determined using the method of Becker et al., *Appl. Microbiol.* 11, 421–423 (1964).

The results of these studies are set forth below.

| Test | Result Observed |
|---|---|
| Diagnostic sugars detected | Glucose, Ribose |
| Isomers of 2,6-diaminopimelic acid | LL-isomer |

A comparison of the characteristics of Culture A47934.1 and *S. toyocaensis* ATCC 19814 is set forth in Table 3, which follows:

TABLE 3

| COMPARISON OF CHARACTERISTICS OF CULTURE A47934.1 AND ATCC 19814 | | |
|---|---|---|
| Characteristic | A47934.1 | ATCC 19814 |
| Aerial spore mass color | Gray | Gray |
| Carbon utilization pattern | + | + |
| (D-mannitol) | − | + |
| (D-xylose) | + | ± |
| Gelatin liquefaction | + | + |
| Melanoid pigment | − | − |
| ISP No. 1 | − | − |
| ISP No. 6 | − | − |
| ISP No. 7 | − | − |
| ISP No. 7 mod. | − | ND |

TABLE 3-continued

COMPARISON OF CHARACTERISTICS OF
CULTURE A47934.1 AND ATCC 19814

| Characteristic | A47934.1 | ATCC 19814 |
|---|---|---|
| Morphology | S | S |
| NaCl tolerance - percent | 9 | ND |
| Nitrate reduction | + | + |
| Reverse side color | Y—Br | Y—Br |
| Skim milk hydrolyzed | ± | + |
| Soluble pigments | — | — |
| Spore shape | Oblong | Oblong |
| Spore surface | Spiny | Spiny |
| Starch hydrolysis | + | + |
| Temperature range - °C. | 15–40 | ND |

ND = not done

A summary of the similarities and differences of Culture A47934.1 and *Streptomyces toyocaensis* ATCC 19814 is set forth in Table 4, which follows:

TABLE 4

SUMMARY OF CULTURE A47934.1
AND *S. TOYOCAENSIS* ATCC 19814

| Similarities | Differences |
|---|---|
| Aerial spore mass color (GY) | Utilization of mannitol and xylose by *S. toyocaensis* |
| Carbon utilization pattern | |
| Distinctive pigments absent | |
| Gelatin liquefaction | |
| Melanoid pigments absent | |
| Morphology (S) | |
| Nitrate reduction | |
| Skim milk action | |
| Soluble pigments absent | |
| Spore chain length (10–50) | |
| Spore surface ornamentation (Spy) | |
| Starch hydrolysis | |

Culture A47934.1 has been deposited and made a part of the stock culture collection of the Northern Regional Research Center, U.S. Department of Agriculture, Agricultural Research Service, Peoria, Ill. 61604, from which it is available to the public under the number NRRL 15009.

Antibiotic A47934 is acidic, as it contains both a carboxylic acid function and an —SO₃H function, and is therefore readily capable of forming salts with bases. The antibiotic also contains an amino group which will form salts only with strong acids having pH 3 or less. The pharmaceutically-acceptable salts so formed are also part of this invention. "Pharmaceutically-acceptable" salts are salts in which the toxicity of the compound as a whole toward warm-blooded animals is not increased relative to the non-salt form. Representative and suitable salts of antibiotic A47934 include those addition salts formed by standard reaction of the carboxylic acid function and —SO₃H function with such bases as sodium hydroxide, sodium carbonate, potassium carbonate, calcium hydroxide, potassium hydroxide, trimethylamine, ammonium hydroxide, diethanolamine, and like bases, as well as salts formed by reaction of the amino group with acids having a pH of 3 or less, such as sulfuric, hydrochloric, and phosphoric.

Antibiotic A47934 is active against gram positive microorganisms. This antibiotic also shows activity for growth promotion and improving feed efficiency in poultry, swine, and cattle.

The levels at which antibiotic A47934 inhibits the growth of organisms were determined using various testing procedures.

Antibiotic A47934 has been tested and found to be active against a number of anaerobic bacteria, as recorded in Table 5, which follows, the MIC values having been determined by the agar dilution method.

TABLE 5

ACTIVITY OF ANTIBIOTIC A47934 AGAINST
ANAEROBIC BACTERIA

| Test Organism | MIC (μg./ml.) |
|---|---|
| *Clostridium difficile* 2994 | 0.5 |
| *Clostridium perfringens* 81 | 0.5 |
| *Clostridium septicum* 1128 | 0.5 |
| *Eubacterium aerofaciens* 1235 | 1.0 |
| *Peptococcus asaccharolyticus* 1302 | 0.5 |
| *Peptococcus prevoti* 1281 | 1.0 |
| *Peptostreptococcus anaerobius* 1428 | 0.25 |
| *Peptostreptococcus intermedius* 1264 | 1.0 |
| *Propionibacterium acnes* 79 | 1.0 |
| *Bacteroides fragilis* 111 | 32.0 |
| *Bacteroides fragilis* 1877 | 32.0 |
| *Bacteroides fragilis* 1936B | 32.0 |
| *Bacteroides thetaiotaomicron* 1438 | 32.0 |
| *Bacteroides melaninogenicus* 1856/28 | >128.0 |
| *Bacteroides melaninogenicus* 2736 | 16.0 |
| *Bacteroides vulgatis* 1211 | 32.0 |
| *Bacteroides corrodens* 1874 | 32.0 |
| *Fusobacterium symbiosum* 1470 | 2.0 |
| *Fusobacterium necrophorum* 6054A | 0.25 |

Antibiotic A47934 is also against a number of strains of *Clostridium difficile*, as determined by the agar-dilution method. The results of the tests are recorded in Table 6, which follows.

TABLE 6

ACTIVITY OF ANTIBIOTIC A47934
AGAINST *CLOSTRIDIUM DIFFICILE* STRAINS

| *Clostridium difficile* | MIC (μg./ml.) |
|---|---|
| 8484 | ≦0.5 |
| 6890 | ≦0.5 |
| 2634 | ≦1.0 |
| 78 | ≦0.5 |
| A-194 | ≦0.5 |
| A-195 | ≦0.5 |
| A-196 | ≦0.5 |
| A-279 | ≦1.0 |
| A-280 | ≦0.5 |
| A-281 | ≦0.5 |
| WAL-2112 | ≦0.5 |
| WAL-3657 | ≦0.5 |
| WAL-4268 | ≦0.5 |
| 107B | ≦0.5 |
| 111F | ≦0.5 |
| 1153 | ≦0.5 |
| 3424-5B | ≦0.5 |
| 3816 | ≦0.5 |
| 3950D | ≦0.5 |

Antibiotic A47934 exhibits activity against a number of gram-positive pathogenic bacteria, as determined by standard agar-dilution assays. The MIC values so determined are shown in Table 7, which follows.

TABLE 7

ACTIVITY OF ANTIBIOTIC A47934
AGAINST A VARIETY OF BACTERIA

| Organism | MIC (μg./ml.) |
|---|---|
| *Staphylococcus aureus* X1.1 | 0.06 |
| *Staphylococcus aureus* V41 | 0.125 |
| *Staphylococcus aureus* X400 | 0.25 |
| *Staphylococcus aureus* S13E | 0.125 |
| *Staphylococcus epidermidis* EPI1 | 0.25 |
| *Staphylococcus epidermidis* EPI2 | 2.0 |
| *Streptococcus pyogenes* C203 | 0.25 |
| *Streptococcus pneumoniae* Park 1 | 0.06 |
| Streptococcus Group D X66 | 0.5 |
| Streptococcus Group D 9960 | 0.5 |
| *Haemophilus influenza* C.L. | 2.0 |

TABLE 7-continued
ACTIVITY OF ANTIBIOTIC A47934 AGAINST A VARIETY OF BACTERIA

| Organism | MIC (µg./ml.) |
|---|---|
| Haemophilus influenza 76 | 4.0 |
| Shigella sonnei N9 | >128.0 |
| Escherichia coli N10 | >128.0 |
| Escherichia coli EC14 | >128.0 |
| Escherichia coli TEM | >128.0 |
| Klebsiella pneumoniae X26 | >128.0 |
| Klebsiella pneumoniae KAE | >128.0 |
| Klebsiella pneumoniae X68 | >128 |
| Enterobacter aerogenes C32 | >128 |
| Enterobacter aerogenes EB17 | >128 |
| Enterobacter cloacae EB5 | >128 |
| Enterobacter cloacae 265A | >128 |
| Salmonella typhi X514 | >128 |
| Salmonella typhi 1335 | >128 |
| Pseudomonas aeruginosa X528 | >128 |
| Pseudomonas aeruginosa X239 | >128 |
| Pseudomonas aeruginosa Ps18 | >128 |
| Pseudomonas aeruginosa Ps72 | >128 |
| Serratia marcescens X99 | >128 |
| Serratia marcescens SE3 | >128 |
| Proteus morganii PR15 | >128 |
| Proteus inconstans PR33 | >128 |
| Proteus rettgeri PR7 | >128 |
| Proteus rettgeri C24 | >128 |
| Citrobacter freundii CF17 | >128 |

Antibiotic A47934 has shown in vivo antimicrobial activity against experimental bacterial infections. When two doses of test compound were administered subcutaneously to mice in illustrative infections, the activity is measured as an $ED_{50}$ value [effective dose in mg./kg. to protect fifty persent of the test animals: See Warren Wick, et al., *J. Bacteriol.* 81, 233–235 (1961)]. The $ED_{50}$ values observed for antibiotic A47934 are given in Table 8, which follows.

TABLE 8

| | In Vivo Activity A47934 $ED_{50}$ (mg./kg. × 2) | | |
|---|---|---|---|
| Antibiotic | S. pyogenes C203 | S. pneumoniae (Park I) | S. aureus (3055) |
| A47934 | 3.38 | 1.77 | <0.3 |

Antibiotic A47934, when given intraperitoneally to mice, has an acute toxicity greater than 300 mg./kg.

In one of its aspects, this invention provides a method for treating infections in man or animals which comprises administering to said man or animal a non-toxic antibiotic-effective dose of between about 25 mg. and about 2,000 mg. of antibiotic A47934 or a pharmaceutically-acceptable, non-toxic salt of said antibiotic.

In the treatment of infections in man, the antibiotic is administered by the parenteral route, e.g., by i.m. injection, or i.v. infusion. For injection, the antibiotic, or a pharmaceutically-acceptable salt thereof, is dissolved in a physiologically-acceptable diluent at the desired concentration and administered. Suitable diluents include for example, Water-for-Injection, 0.9% saline, 5% dextrose, Ringer's solution, or other commonly employed diluent. For administration by i.v. infusion, the antibiotic or salt thereof can be made up in a physiological fluid or dilute nutrient at a suitable concentration; for example, at a concentration between about 5% and about 10%, and slowly infused with the fluid. Alternatively, the antibiotic may be administered by the "piggy-back" method.

The antibiotic, or the pharmaceutically-acceptable, non-toxic salts thereof can be made up in dosage unit formulations in hermetically sealed vials, sterile, rubber-stoppered vials, or in plastic pouches. Such unit dosage forms can contain excipients such as antioxidants, solubilizing agents, dispersing agents, buffers, and the like. One such dosage unit formulation comprises 100 mg. of A47934 antibiotic, or a pharmaceutically-acceptable salt thereof, in a rubber (butyl rubber) stoppered vial. Another dosage unit formulation comprises 250 mg. of antibiotic A47934, or a salt thereof, in a sterile, sealed vial. For i.v. infusion, a dosage unit formulation of this invention comprises 5 g. of antibiotic A47934, or a pharmaceutically-acceptable salt thereof, in a plastic pouch.

When antibiotic A47934 is used as an antibacterial agent, it may be administered either orally or parenterally. As will be appreciated by those skilled in the art, the A47934 antibiotic is commonly administered together with a pharmaceutically-acceptable carrier or diluent. The dosage of A47934 antibiotic will depend upon a variety of considerations, such as, for example, the nature and severity of the particular infection to be treated. Those skilled in the art will recognize that appropriate dosage ranges and/or dosage units for administration may be determined by considering the MIC and $ED_{50}$ values and toxicity data herein provided, together with factors such as the patient or host, and the infecting organism.

The A47934 antibiotic is useful for suppressing the growth of *Clostridium difficile* organisms, which cause pseudomembranous colitis in the intestine. The antibiotic could be used in the treatment of pseudomembranous colitis by the oral administration of an effective dose of said antibiotic or a pharmaceutically-acceptable, non-toxic salt thereof, prepared in a pharmaceutically-acceptable dosage form. For such use, the antibiotic can be administered in gelatin capsules or in liquid suspension.

The antibiotic of this invention also can be used in veterinary medicine in the treatment of infectious diseases, such as mastitis, in domestic and farm animals. The A47934 antibiotic is useful also in animal husbandry, e.g., in enhancing the growth of beef cattle and other ruminants. These uses are further aspects of this invention which are described in more detail in the following paragraphs.

It has been found that antibiotic A47934 is effective in modifying the ratio of volatile fatty acids (VFA) produced in the rumen of ruminant animals having a developed rumen function, and thus antibiotic A47934 has the ability to improve the efficiency of feed utilization in such animals.

It is known that the efficiency of carbohydrate utilization in ruminants is increased by treatments which stimulate the animals' rumen flora to produce propionate compounds rather than acetate or butyrate compounds (for a more complete discussion, see Church et al. in "Digestive Physiology and Nutrition of Ruminants," Vol. 2, 1971, pp. 622 and 625).

Test 1

The effectiveness of antibiotic A47934 in modifying the ratio of volatile fatty acids produced in the rumen has been determined using the in vitro test described in Raun, U.S. Pat. No. 3,928,571 (Dec. 23, 1975), see the EXAMPLE therein. The results of the test as carried out on antibiotic A47934 are recorded in Table 9.

The data in Table 9, which follows, are reported as the ratio of VFA's produced in treated flasks to VFA's produced in untreated control flasks. This method of reporting the data shows most clearly the results of the changes in the chemistry of the rumen brought about by the present novel method of feed utilization improvement.

TABLE 9

| Compound | Rate | Acetate | Propionate | Butyrate |
|---|---|---|---|---|
| A47934 | 4 mcg./ml. | 0.81 | 1.32 | 1.03 |
| A47934 | 10 mcg./ml. | 0.95 | 1.12 | 1.00 |
| A47934 | 2 mcg./ml. | 1.09 | 1.10 | 1.03 |
| A47934 | 1 mcg./ml. | 0.99 | 1.11 | 1.01 |

The results tabulated above show that antibiotic A47934 is effective in increasing propionate production in the rumen.

Administration of the antibiotic compound useful in this method prevents and treats ketosis as well as improving feed utilization. The causative mechanism of ketosis is a deficient production of propionate compounds. A presently recommended treatment is administration of propionic acid or feeds which preferentially produce propionates. It is obvious that the method of this application, which method encourages propionate production from ordinary feeds, will reduce incidence of ketosis.

As antibiotic A47934 is closely related structurally to antibiotic A41030 factor A, which factor A is useful in improving milk production in lactating animals having a developed rumen process, it is to be expected that antibiotic A47934 will also have this utility.

It has been found that the antibiotic compound disclosed herein increases the efficiency of feed utilization in ruminant animals. The easiest way to administer the antibiotic is by mixing it in the animal's feed.

Thus, the A47934 antibiotic can be readily mixed with conventional dairy feed compositions. Such compositions are then fed to the livestock according to art-recognized methods.

Conventional feeds for dairy animals include various grains and mixtures of grains such as corn and oats, and roughage feeds such as hay, cottonseed hulls, rice hulls, silage, and the like. The A47934 antibiotic can be mixed with such feed compositions at a rate of about 30 to about 300 grams per ton of feed (on a dry matter basis).

For commercial utilization of antibiotic A47934 for improved milk production according to this aspect of the invention, it is desirable to employ the active ingredient as a feed additive premix or a feed additive concentrate. In such formulations, the antibiotic A47934 is uniformly distributed throughout a conventional organic or inorganic animal feed carrier such as ground corn, barley, soybean meal, wheat, soy flour, or similar low-priced edible ingredient. The premix is then mixed uniformly with the normal daily feed ration prior to feeding the ration to the lactating ruminant. The premix is added at a rate sufficient for the animal to receive a propionate-increasing amount of antibiotic A-47934.

The following composition is a typical ration to be administered to lactating ruminants, to which ration a milk-production-increasing quantity of A47934 is added.

| Ingredient | Percent by Weight |
|---|---|
| Corn | 32.15 |
| Barley | 10.0 |
| Molasses | 7.5 |
| Oats | 10.0 |
| Soybean oil meal (48% protein) | 13.8 |
| Beet pulp | 2.5 |
| Corn gluten feed | 12.5 |
| Distillers grain | 7.5 |
| Trace mineral mix | 0.05 |
| Salt | 1.0 |
| Dicalcium phosphate | 2.0 |
| | 100.00 |

The above ingredients are blended to uniformity and then antibiotic A47934 is added in such amount that the lactating ruminants, in this instance cows, would receive about 600 mg./head/day.

However, the antibiotic compound can be usefully administered in other ways. For example, it can be incorporated into tablets, drenches, boluses, or capsules, and dosed to the animals. Formulation of the antibiotic compound in such dosage forms can be accomplished by means of methods well known in the veterinary pharmaceutical art. Each individual dosage unit should contain a quantity of the feed-efficiency-improving compound which has a direct relation to the proper daily dose for the animal to be treated.

Capsules are readily produced by filling gelatin capsules with any desired form of the antibiotic. If desired, the antibiotic can be diluted with an inert powdered diluent, such as a sugar, starch, or purified crystalline cellulose in order to increase its volume for convenience in filling capsules.

Tablets of the antibiotic used in this novel method are made by conventional pharmaceutical processes. Manufacture of tablets is a well-known and highly-advanced art. In addition to the active ingredient, a tablet usually contains a base, a disintegrator, an absorbent, a binder, and a lubricant. Typical bases include lactose, fine icing sugar, sodium chloride, starch and mannitol. Starch is also a good disintegrator, as is alginic acid. Surface-active agents such as sodium lauryl sulfate and dioctyl sodium sulphosuccinate are also sometimes used. Commonly used absorbents again include starch and lactose, while magnesium carbonate is also useful for oily substances. Frequently-used binders are gelatin, gums, starch, dextrin and various cellulose derivatives. Among the commonly-used lubricants are magnesium stearate, talc, paraffin wax, various metallic soaps, and polyethylene glycol.

This novel method can also be practiced by the administration of the antibiotic compound as a slow-payout bolus. Such boluses are made as tablets are made, except that a means to delay the dissolution of the antibiotic is provided. Boluses are made to release for lengthy periods. The slow dissolution is assisted by choosing a highly water-insoluble form of the antibiotic. A substance such as iron filings is added to raise the density of the bolus and keep it static on the bottom of the rumen.

Dissolution of the antibiotic is delayed by use of a matrix of insoluble materials in which the drug is embedded. For example, substances such as vegetable waxes, purified mineral waxes, and water-insoluble polymeric materials are useful.

Drenches of the antibiotic are prepared most easily by choosing a water-soluble form of the antibiotic. If an insoluble form is desired for some reason, a suspension may be made. Alternatively, a drench may be formulated as a solution in a physiologically-acceptable solvent such as a polyethylene glycol.

Suspensions of insoluble forms of the antibiotic can be prepared in nonsolvents such as vegetable oils such as peanut, corn, or sesame oil; in a glycol such as propylene glycol or a polyethylene glycol; or in water, depending on the form of the antibiotic chosen.

Suitable physiologically-acceptable adjuvants are necessary in order to keep the antibiotic suspended. The adjuvants can be chosen from among the thickeners, such as carboxymethylcellulose, polyvinylpyrrolidone, gelatin, and the alginates. Many classes of surfactants also serve to suspend antibiotics. For example, lecithin alkylphenol polyethylene oxide adducts, naphthalenesulfonates, alkylbenzenesulfonates, and the polyoxyethylene sorbitan esters are useful for making suspensions in liquid nonsolvents.

In addition, many substances which affect the hydrophilicity, density, and surface tension of the liquid can assist in making suspensions in individual cases. For example, silicone antifoams, glycols, sorbitol, and sugars can be useful suspending agents.

The suspendable antibiotic may be offered to the animal grower as a suspension, or as a dry mixture of the antibiotic and adjuvants to be diluted before use.

In the preparation of dusts or powders for administration by insufflation, the antibiotics are typically mixed with talc, diatomaceous earth, or some other inert substance as an adjuvant.

The antibiotic may also be administered in the drinking water of the ruminants. Incorporation into drinking water is performed by adding a water-soluble or water-suspendable form of the antibiotic to the water in the proper amount. Formulation of the antibiotic for addition to drinking water follows the same principles as formulation of drenches.

The most practical way to treat animals with this antibiotic compound is by the formulation of the compound into the feed supply. Any type of feed may be medicated with the antibiotic compound, including common dry feeds, liquid feeds, and pelleted feeds.

For use in animal feeds, the culture solids, including fermentation medium constituents and mycelium, can be used without extraction or separation, but preferably after removal of water, as a source of the A47934 antibiotic. For example, after production of AA47934 antibiotic activity, the whole fermentation broth can be filtered and the filter cake containing the A47934 dried. In addition, the dried mycelium cake can be extracted with an aqueous alkaline solution at pH 10.5, the extract neutralized, and the extract dried to obtain the A47934 antibiotic. Also, the whole fermentation broth can be dried by lyophilization, by drum drying, or by azeotropic distillation and drying. The dried broth is then mixed directly into the feed premix.

The methods of formulating drugs into animal feeds are well known. It is usual to make a concentrated drug premix as a raw material for medicated feeds. For example, typical drug premixes may contain from about one to about 400 grams of drug per pound of premix. The wide range results from the wide range of concentration of drug which may be desired in the final feed. Premixes may be either liquid or solid.

The formulation of animal feeds containing the proper amounts of the antibiotic compound for useful treatment is mainly a matter of arithmetic. It is necessary only to calculate the amount of compound which it is desired to administer to each animal, to take into account the amount of feed per day which the animal eats, and the concentration of antibiotic compound in the premix to be used, and calculate the proper concentration of antibiotic compound in the feed.

All of the methods of formulating, mixing, and pelleting feeds which are normally used in the ruminant or nonruminant feed art are entirely appropriate for manufacturing feeds containing the antibiotic compound.

It is not intended to limit the scope of this aspect of the invention to any particular formulations or methods of administration. This aspect of the invention is a method of increasing the efficiency of feed utilization by ruminant animals by the oral administration of certain antibiotics. However the administration may be accomplished, it is regarded as coming within the scope of the invention.

Antibiotic A47934 is closely related in its structure to antibiotic A41030 factor A, and thus would be expected to possess many of the same utilities. This antibiotic A47934 has shown activity as a growth promoter in chickens, the test being carried out as follows:

Test 2

Chicks, 8-day old Penobscot broilers, were used in this test. A total of 560 chicks were used divided into groups of 7 birds each. There were 35 groups acting as controls and 5 groups were treated with the antibiotic added to the broiler starter ration at the rate of 20 g. of antibiotic A47934 per ton of feed. The broiler starter ration has the following composition:

| Broiler Starter Ration | | | |
|---|---|---|---|
| Ingredient | Percent | AMT/ 80 LBS | AMT/ 3000 LBS |
| Corn, yellow ground | 65.5 | 52.42 | 1965.9 |
| Soybean meal, solvent extracted dehulled (49%) | 25.36 | 20.29 | 760.8 |
| Beef tallow | 5.00 | 4.00 | 150.0 |
| Dicalcium phosphate, feed grade | 2.15 | 1.72 | 64.5 |
| Limestone | 0.83 | 0.66 | 24.9 |
| Trace mineral premix TK-01 (1.02)[1] | 0.10 | 0.08 | 3.0 |
| Salt | 0.35 | 0.28 | 10.5 |
| Vitamin premix TK-04 (1.00)[2] | 0.50 | 0.40 | 15.0 |
| Methionine hydroxy analog | 0.18 | 0.14 | 5.4 |
| | 100.00 | 79.99 | 3000.0 |

[1]Trace mineral premix provides 75 mg of manganese, 50 mg of zinc, 25 mg of iron and 1 mg of iodine per kg of complete feed.
[2]Vitamin premix provides 3000 IU of vitamin A, 900 ICU of vitamin D, 40 mg of vitamin E, 0.7 mg of vitamin K, 1000 mg of choline, 70 mg of niacin, 4 mg of pantothenic acid, 4 mg of riboflavin, 100 mcg of vitamin $B_{12}$, and 100 mcg of biotin per kg of complete feed.

| CALCULATED ANALYSIS | |
|---|---|
| Protein, % | 18.00 |
| Met. Energy, KCal/kg | 3239 |
| ME/P Ratio 179.94 | (81.79) |
| Fat, % | 7.37 |
| Fiber, % | 2.66 |
| Ash, % | 5.14 |
| Calcium, % | 0.85 |
| Phosphorus, % | 0.73 |
| Avail. Phosphorus, % | 0.50 |
| Manganese, mg/kg | 85 |
| Iron, mg/kg | 72 |
| Copper, mg/kg | 11 |
| Zinc, mg/kg | 72 |
| Selenium, mcg/kg | 74 |
| Magnesium, mg/kg | 1693 |
| Potassium, mg/kg | 7158 |
| Sodium, mg/kg | 1682 |
| Iodine, mg/kg | 1 |

-continued

| CALCULATED ANALYSIS | | |
|---|---|---|
| Vitamin A, IU/kg | | 5162 |
| Vitamin D, ICU/kg | | 900 |
| Vitamin E, mg/kg | | 56.2 |
| Vitamin K, mg/kg | | 0.7 |
| Choline, mg/kg | | 1450 |
| Niacin, mg/kg | | 85 |
| Pantothenic acid, mg/kg | | 11.1 |
| Vitamin $B_6$, mg/kg | | 7.5 |
| Riboflavin, mg/kg | | 5.5 |
| Thiamine, mg/kg | | 2.8 |
| Folic acid, mg/kg | | 1.1 |
| Vitamin $B_{12}$, mcg/kg | | 100 |
| Biotin, mcg/kg | | 233 |
| Arginine, % | 1.305 | (7.25)[3] |
| Lysine, % | 0.956 | (5.31) |
| Glycine, % | 0.901 | (5.01) |
| Methionine, % | 0.433 | (2.41) |
| Cystine, % | 0.273 | (1.52) |
| Total Sulfur Amino acids, % | 0.706 | (3.92) |
| Tryptophan, % | 0.252 | (1.40) |
| Linolieic acid, % | | 1.25 |

[3]Values in parenthesis represent the amino acids expressed as a percent of dietary protein.

Feed and water were available to all groups ad libitum for 21 days. Two time replicates were run. The criteria for activity: 3% increase in weight gain and/or 2% improvement in feed efficiency in one or both time replicates. The results are set forth in Table 10, which follows:

TABLE 10

| Treatment | Conc. g./T. | Weight Gain gm. | Weight Gain % Impr. | Feed Efficiency F/G | Feed Efficiency % Impr. |
|---|---|---|---|---|---|
| Control | — | 484 | — | 1.791 | |
| A47934 | 20 | 519 | 7.23 | 1.707 | 4.69 |
| Control | — | 464 | — | 1.748 | |
| A47934 | 20 | 464 | 0 | 1.746 | — |

F/G = Total feed consumed divided by total weight gain.

The data indicate a good response to A47934 in the first experiment and no response in the second. The lack of response in the second experiment can be attributed to the lack of response in one of the five cages assigned to the treatment.

Alternatively the antibiotic A47934, in the form of a pharmaceutically-acceptable, non-toxic salt can be administered in the drinking water of the chickens.

The A47934 antibiotic thus can be used as a growth promoter in chickens when administered to chickens in their diet at the rate of from about 5 to about 30 g. of A47934, or a pharmaceutically-acceptable, non-toxic salt thereof, per ton of feed.

Antibiotic A47934, because of its close structural relationship to antibiotic A41030 factor A, also can be expected to act as a growth promoter when administered to weanling pigs. This activity is demonstrated in Test 3, which follows.

Test 3

Antibiotic A47934 was tested at levels of 10 and 50 ppm. in the diet of pigs initially weighing an average of about 23 pounds, compared with Tylan ® (tylosin, Elanco) administered in the diet at 110 ppm. The experiment was conducted in an environmentally controlled nursery facility with wire mesh floors in the pens. There were four replicates per treatment and four pigs per replicate for the 28-day experiment. There were six replicates of four pigs per replicate in the control group, which group received the unmedicated diet. The pigs were fed ad libitum on an 18 percent protein corn-soy ration having the following composition:

| INGREDIENTS | Swine Ration PERCENT | LBS./TON |
|---|---|---|
| Corn, yellow, ground | 66.35 | 1327 |
| Soybean oil meal, solvent extracted dehulled, 50% | 19.35 | 387 |
| Skimmed milk, dried | 10.00 | 200 |
| Calcium carbonate | 1.20 | 24 |
| Dicalcium phosphate, feed grade | 1.20 | 24 |
| Salt | 0.50 | 10 |
| Trace mineral premix, AN-03[1] | 0.10 | 2 |
| Swine vitamin premix, SW-03[2] | 1.00 | 20 |
| Vitamin A premix, 3M USP units/lb.[3] | 0.05 | 1 |
| Methionine Hydroxy Analogue, 93% | 0.20 | 4 |
| Selenium Premix[4] | 0.05 | 1 |
| | 100.00 | 2000 |

[1]Each kg of premix contains the following: 50 g manganese as manganese sulfate; 100 g zinc as zinc carbonate; 50 g iron as ferrous sulfate; 5 g copper as copper oxide; 1.5 g iodine as potassium iodide and 150 g maximum and 130 g minimum calcium as calcium carbonate.
[2]Each kg of premix contains the following: 77,161 IU Vitamin $D_2$; 2,205 IU Vitamin E; 411 mg riboflavin; 1,620 mg pantothenic acid; 2,205 mg niacin; 4.4 mg Vitamin $B_{12}$; 441 mg Vitamin K; 19,180 mg choline; 110 mg folic acid; 165 mg pyridoxine; 110 mg thiamine; 22 mg biotin.
[3]Each kg of premix contains 6,613,800 IU Vitamin A.
[4]Each kg of premix contains 200 mg of selenium as sodium selenite. The calculated analysis is added selenium only.

| CALCULATED ANALYSIS | |
|---|---|
| Crude Protein % | 19.10 |
| Ether Extract % | 2.83 |
| Crude Fiber % | 1.89 |
| Ash % | 5.60 |
| Calcium % | 0.90 |
| Phosphorus % | 0.65 |
| Dig. E. KCal/kg | 3545.59 |
| Met. E. KCal/kg | 3270.00 |
| Ribofl. mg/kg | 7.88 |
| Niacin mg/kg | 27.38 |
| Pant. Acid mg/kg | 24.96 |
| Choline mg/kg | 1224.95 |
| Vitamin $B_{12}$ mcg/kg | 50.54 |
| Folic Acid mg/kg | 1.99 |
| Pyridoxine mg/kg | 8.37 |
| Thiamine mg/kg | 4.30 |
| Biotin mg/kg | 0.35 |
| Vitamin D IU/kg | 811.61 |
| Vitamin A IU/kg | 3904.05 |
| Vitamin E IU/kg | 23.61 |
| Vitamin K mg/kg | 4.41 |
| Copper mg/kg | 15.43 |
| Iron mg/kg | 98.12 |
| Iodine mg/kg | 1.50 |
| Magnesium mg/kg | 1627.70 |
| Zinc mg/kg | 119.61 |
| Manganese mg/kg | 61.74 |
| Selenium mg/kg | 0.10[4] |
| Lysine % | 1.02 |
| Methionine % | 0.53 |
| Cystine % | 0.29 |
| Tryptophan % | 0.23 |
| Isoleucine % | 1.03 |
| Arginine % | 1.15 |
| Histidine % | 0.44 |
| Leucine % | 1.72 |
| Penylalanine % | 0.97 |
| Tyrosine % | 0.52 |
| Threonine % | 0.77 |
| Valine % | 0.98 |

At the end of the trial, the average weight of the individual pig had increased to 53 pounds. The results of the trial are reported in Table 11, which follows:

TABLE 11

| Treatment | Level ppm | ADG lbs. | % Increase | ADF lbs. | % Increase | F/G | % Improvement |
|---|---|---|---|---|---|---|---|
| Control | 0 | 0.97 | | 1.89 | | 1.97 | |
| A47934 | 10 | 1.00 | 3.1 | 1.83 | −3.2 | 1.82 | 7.6 |
| A47934 | 50 | 1.07 | 10.3 | 1.98 | 4.7 | 1.85 | 6.1 |
| Tylan | 110 | 1.01 | 4.1 | 1.94 | 2.6 | 1.92 | 2.5 |

ADG = average daily gain
ADF = average daily feed consumption
F/G = ratio of feed consumption to gain Thus, in another aspect, this invention provides a method for promoting the growth of weanling pigs which comprises administering to the pigs in their diet between about 10 and about 50 ppm. of the A47934 antibiotic, or a pharmaceutically-acceptable, nontoxic salt thereof. The A47934 antibiotic, in the form of a pharmaceutically-acceptable, non-toxic salt, could also be administered to the pigs in the drinking water.

In addition to the utility of A47934 in promoting the growth of weanling pigs, it is to be expected by those skilled in the art that antibiotic A47934 will be useful for promoting the growth of pigs of varying sizes, including those of marketing size, i.e., those pigs weighing about 200 pounds.

It is usual to treat economic animals, including ruminants, with a variety of growth promoters, disease-preventives, and disease treatments throughout their lives. Such drugs are often used in combination. The instant method may be practiced in combination with other treatments.

As shown by the above results, antibiotic A47934 beneficially alters the production of acetates in the rumen. The same treatment also benefits monogastric animals which ferment fibrous vegetable matter in the cecum. The monogastric animals here referred to are those which consume fibrous vegetable food and digest at least part of it by microbiological fermentation in the cecum. The cecal fermentation follows a chemical pathway similar to rumen fermentation.

Horses, swine, and rabbits are exemplary animals which digest a part of their food by cecal fermentation. The overall feed utilization of such animals is improved by the oral administration of these antibiotics which cause a beneficial change in the propionate/acetate ratio. Horses and rabbits are exemplary of animals in which cecal fermentation is a major part of the total digestive process, and in which these antibiotics are accordingly particularly beneficial.

The A47934 antibiotic is produced by culturing *Streptomyces toyocaensis* NRRL 15009, or an A47934-producing mutant or variant thereof, in a culture medium containing assimilable sources of carbon, nitrogen, and inorganic salts, under submerged aerobic fermentation conditions, until a substantial amount of antibiotic activity is produced.

As is the case with other organisms, the characteristics of the A47934-producing culture, NRRL 15009, are subject to variation. For example, natural variants, mutants (spontaneous or induced), transconjugants and recombinants (including recombinant DNA on plasmids) of the NRRL 15009 strain, or derived from this strain, which produce the A47934 antibiotic may be used in this invention.

A number of different media may be used to produce antibiotic A47934 with *Streptomyces toyocaensis* NRRL 15009. For economy in production, optimal yield, and ease of product isolation, however, certain culture media are preferred. These media should contain assimilable sources of carbon, nitrogen, and inorganic salts. Suitable carbon sources include glucose, potato dextrin, tapioca dextrin, corn starch, and molasses. Suitable nitrogen sources include soybean grits, acidhydrolyzed casein, beef extract, and soybean meal.

Essential trace elements necessary for the growth and development of the organism can be obtained using corn steep liquor, and may occur as impurities in other constituents of the media in amounts sufficient to meet the growth and biosynthetic requirements of the organism. However, it may be beneficial to incorporate in the culture media additional soluble nutrient inorganic salts capable of yielding sodium, potassium, magnesium, calcium, ammonium, chloride, carbonate, phosphate, sulfate, nitrate and like ions.

For producing substantial quantities of antibiotic A47934, employing NRRL 15009, submerged aerobic fermentation in tanks is utilized. However, small amounts of antibiotic A47934 may be obtained by shakeflask culture. For tank fermentation, it is preferable to use a vegetative inoculum. The vegetative inoculum is prepared by inoculating a small volume of culture medium with the spore form, mycelial fragments, or a lyophilized pellet of the organism to obtain a fresh, actively growing culture of the organism. The vegetative inoculum is then transferred to a larger tank where, after a suitable incubation time, the A47934 antibiotic is produced in optimal yield.

The pH of the uninoculated fermentation medium varies with the medium used for production, but the pH of all of the fermentation media falls in the range of from about pH 6.4 to about 7.0.

This A47934-producing organism can be grown over a broad temperature range of from about 20° to about 40° C. Optimum production of antibiotic A47934 with NRRL 15009 appears to occur at a temperature of about 30° C.

As is customary in aerobic submerged culture processes, sterile air is dispersed through the culture medium. For efficient growth of the organism, the volume of air used in tank production is in the range of from about 0.1 to about 0.5 volume of air per volume of culture medium per minute (v/v/m). An optimum rate in a 165-liter vessel is about 0.25 v/v/m with agitation provided by conventional impellers rotating at about 250 RPM. It may be necessary to add small amounts (i.e. 0.2 ml./L.) of an antifoam agent such as propylene glycol to large-scale fermentation media if foaming becomes a problem.

Production of the A47934 antibiotic can be monitored during the fermentation by either agar diffusion, i.e., the agar well plate test, or by turbidimetric methods. The test organism employed was *Bacillus subtilis* ATCC 6633. The whole broth sample is adjusted to pH 10.5 with aqueous sodium hydroxide and centrifuged before assaying.

Antibiotic activity is generally present after about 36 hours and remains present for at least 7 or more days during the fermentation period. Peak antibiotic production occurs in from about 4 to about 5 days fermentation time.

The A47934 antibiotic can be recovered from the fermentation medium by methods used in the art. As most of the A47934 antibiotic is adsorbed onto/or in the cells, the whole fermentation broth is adjusted to about pH 10.5 with aqueous base, suitably aqueous sodium hydroxide, to release the antibiotic from the cells. Diatomaceous earth (Hyflo Super-cel, JohnsManville Corp.) is added as a filter aid and the mixture stirred and then filtered, suitably using a filter press. The filtrate, which contains the antibiotic activity is adjusted to neutral pH, i.e., pH 7.0, mixed with Diaion HP-20 (a highly porous styrenedivinylbenzene copolymer in bead form, available from Mitsubishi Chemical Industries, Ltd., Tokyo, Japan), and stirred for a period of time, such as about 60 minutes. The aqueous phase is then separated from the resin, upon which the antibiotic activity is adsorbed, by aspiration or filtration. Other suitable adsorbents include carbon, silica gel, polyamide, alumina, macroreticular resins (XAD-2, XAD-4, etc.), and ion exchange resins, particularly anion exchange resins (e.g., IRA 68, Dowex 1), all known to the art.

The HP-20 resin, bearing the adsorbed A47934 activity, is washed with water and water:methanol (4:1), and filtered. The antibiotic activity is then eluted from the resin using water:methanol (1:1) as the eluting agent. The eluate is concentrated and lyophilized to give crude A47934 as a light brown powder, which can be further purified by chromatographic procedures known to those of ordinary skill in the art.

Antibiotic A47934 can also be removed from the broth filtrate by adjusting such filtrate to about pH 3 with acid, for complete precipitation, followed by filtration. A47934 starts to precipitate at about pH 6.5 and is complete at about pH 3. Inorganic acids such as hydrochloric, sulfuric, and phosphoric, and organic acids such as acetic acid and formic acid are suitable for acidification. The crude A47934 thus obtained can be further purified by chromatographic procedures.

In order to illustrate more fully the operation of this invention, the following examples are provided.

EXAMPLE 1

Preparation of First Stage Inoculum

A medium was prepared for use in the agar slant culture of *Streptomyces toyocaensis* NRRL 15009:

| Ingredient | Amount (g./L.) |
|---|---|
| Tomato paste | 20.0 |
| Precooked oatmeal | 20.0 |
| Agar | 20.0 |
| Deionized water | q.s. to 1.0 liter |

After the above ingredients had been mixed together, the medium so formed had pH 5.0, which was adjusted to pH 6.7 with 5N aqueous sodium hydroxide before sterilization. After being sterilized, the medium had pH 6.5.

Spores of *Streptomyces toyccaensis* NRRL 15009 were inoculated on a nutrient agar slant made up of the above-identified ingredients, and the thus-inoculated slant was incubated for about 10 days at a temperature of 30° C. Lyophiles of the culture were then prepared from the slant, and used to inoculate a seed medium having the following composition:

| Ingredient | Amount (g./L.) |
|---|---|
| Glucose | 15.0 |
| Potato dextrin | 20.0 |
| Soybean grits | 15.0 |
| Yeast extract | 1.0 |
| Corn steep liquor | 10.0 |
| CaCO$_3$ | 2.0 |
| Cold tap water | q.s. to 1.0 liter |

After the above ingredients had been mixed together, the medium so formed had pH 5.6, which was adjusted to pH 6.5 with 5N aqueous sodium hydroxide before sterilization. After being sterilized, the medium had pH 6.5–6.7.

The seed medium, 50 ml., was incubated in a 250-ml. wide-mouth Erlenmeyer flask at about 30° C. for about 48 hours on a shaker rotating through an arc 2 inches in diameter at 250 RPM. This incubated medium is used either to inoculate small fermenters (the inoculum being approximately 1% per volume of medium) or to inoculate a second stage medium for the production of a larger volume of culture.

Fermentation of A47934.1

Incubated second-stage medium (800 ml.) thus prepared was used to inoculate 100 liters of sterile production medium having the following composition:

| Ingredient | Amount (g./L.) |
|---|---|
| Antifoam* | 0.2 |
| Glucose | 25.0 |
| Potato dextrin | 30.0 |
| Molasses | 3.0 |
| Soybean grits | 15.0 |
| Acid-hydrolyzed casein | 1.0 |
| CaCO$_3$ | 2.5 |
| Cold tap water | q.s. to 10.0 liter |

*Dow Corning Antifoam 'A'

After the above ingredients had been mixed together, the medium so formed had pH 6.5, which was adjusted to pH 7.5 with 5N aqueous sodium hydroxide before sterilization. After being sterilized, the medium had pH 6.9.

The inoculated production medium was allowed to ferment in a 165-liter fermentation tank for about 4 to about 4.75 days at a temperature of about 30° C. The fermentation medium was aerated with sterile air at the rate of 0.25 v/v/m and was stirred with conventional agitators at about 200–250 RPM.

EXAMPLE 2

Isolation of A47934

Fermentation broth, 141 liters, was adjusted to pH 10.5 by the addition of aqueous 5 N sodium hydroxide solution, 3% filter aid (Hyflo Super-cel, diatomaceous earth, Johns-Manville Corp.) was added, and the mixture stirred for about 1 hour. The mixture was filtered on a filter press to yield 106 liters of a clear filtrate containing the antibiotic activity. This filtrate was adjusted to pH 7.0 with aqueous 5 N hydrochloric acid, and 10.6 liters of Diaion HP-20 resin (a highly porous styrenedivinylbenzene copolymer in bead form, Mitsubishi Chemical Industries, Limited, Tokyo, Japan) was added to the filtrate. The mixture was stirred for about 60 minutes, and the aqueous phase was separated from the resin by aspiration or filtration.

The resin, with the adsorbed antibiotic activity, was washed batchwise sequentially with 30 liters of water, and then twice with 30 liters of a mixture of water:methanol (4:1) by stirring with each volume of solvent for about 30 minutes and filtering. The washed resin was stirred for about 30 minutes with 30 liters of methanol:water (1:1) and filtered, and the same procedure repeated once more to elute the antibiotic activity from the resin. The methanol:water (1:1) filtrates were combined, concentrated in vacuo to a volume of about 4-5 liters (containing about 6-12% solids) and lyophilized to yield 79.1 g. of a light brown powder identified as crude antibiotic A47934, having a purity of about 30-40%. An overall yield of about 44-49% was obtained.

EXAMPLE 3

Preparation of Crude A47934 by Acidic Precipitation

Four hundred and fifty ml. of fermentation broth of A47934 was adjusted to pH 10.5 to extract the A47934 antibiotic from the mycelium, and the solution filtered. The filtrate containing te A47934 antibiotic was divided into 200-ml. portions, and each portion was adjusted to pH 2.5 with aqueous 5 N hydrochloric acid in order to obtain maximum precipitation. The precipitates were recovered by centrifugation, washed with water, and recentrifuged. The precipitate from one portion was suspended in water and freeze-dried to yield 186 mg. of the water-insoluble crude A47934 (20 percent purity).

The precipitate from the other portion was suspended in 50 ml. of water, adjusted to pH 7.5 with aqueous 5 N sodium hydroxide solution, and freeze dried. A yield of 226 mg. of water-soluble crude A47934 antibiotic was obtained (20 percent purity).

These crude A47934 antibiotic preparations can be purified by known methods, e.g. by use of Diaion HP-20 resin and reverse phase HPLC.

EXAMPLE 4

Purification of Antibiotic A47934 by Reverse Phase Chromatography

Crude antibiotic A47934, 30-40 g., was dissolved in 350 ml. of water:acetonitrile (12:8), at pH 8, and the solution was applied to a Chromatospac 100-unit (Instruments SA, Inc., Metuchen, N.J.) containing 4 liters of reversed phase resin (Whatman Silica gel LP-1/C$_{18}$) equiliberated in water:acetonitrile (86:14) containing 2 g. of ammonium acetate/ liter. The column was developed with the same solvent system after sample application, collecting 400 ml. fractions and monitoring the elution at 254 nm. Each fraction was assayed by analytical HPLC [Zorbax ODS resin (0.25×25 cm. column); water:acetonitrile (82:18) containing 2 g. of ammonium acetate/liter; 225 nm. (aufs 0.2)], and the fractions containing only A47934 were combined (e.g., fractions ranged from 32-60, 37-75, and 51-76 for various crude A47934 lots) and concentrated to a volume of about 1 liter.

The concentrates from eight similar runs were combined, the total volume amounting to 8 liters, and applied to a column containing 2 liters of Diaion HP-20 resin packed in water, which chromatographic operation served to remove the ammonium acetate from the combined concentrates. The column was then washed with 6 liters of water and eluted with 4 liters of water:methanol (4:1) and 6 liters of water:methanol (1:1). The 20% methanol eluate was concentrated to 400 ml. and lyophilized to yield 14.82 g. of highly purified A47934. The 50% methanol eluate was concentrated to 1 liter and lyophilized to yield 55.6 g. of highly purified A47934. An overall yield of 81% was achieved in this desalting step.

EXAMPLE 5

Crystallization of Antibiotic A47934

One gram of the highly purified A47934 was dissolved in 50 ml. of acetonitrile:water (60:40) and additional acetonitrile was added to turbidity. After standing at room temperature for 16 hours, a sticky, dark-colored material which had separated was removed, and more acetonitrile was added to the solution to turbidity.

The crystals which formed on further standing at room temperature were recovered by filtering, washed with acetonitrile, and dried. The crystals weighed 750 mg. The crystals were recrystallized by dissolving them in 50 ml. of acetonitrile:water (60:40) and then 300 ml. of acetonitrile was added with stirring. The crystals which formed on standing were filtered off, washed with acetonitrile, and dried in vacuo. The dried crystals weighed 550 mg. Additional drying at 100° C. in vacuo produced an 11% loss in weight due to volatile solvates.

EXAMPLE 6

Preparation of the Monosodium Salt of A47934

To 16 ml. of an aqueous solution of 130 mg. of A47934 (0.1 mole, pH 4.8) was added 0.4 ml. of sodium hydroxide at 10 mg./ml. (0.1 mole). The pH of the final solution was 7.2. The solution was freeze-dried to yield 153 mg. of the monosodium salt of A47934 (Na=2.4%)

EXAMPLE 7

Preparation of the Disodium Salt of A47934

Eight-tenths ml. of sodium hydroxide at 10 mg./ml. water (equivalent to 0.2 mole) was added to 16 ml. of an aqueous solution of 130 mg. of A47934 (0.1 mole, pH 4.8) with stirring; final pH of 8.1. The solution was freeze-dried to yield 156 mg. of the disodium salt of A47934 (Na=3.6%).

EXAMPLE 8

Preparation of the Monopotassium Salt of A47934

Potassium hydroxide solution, 0.56 ml. (10 mg./ml., 0.1 mole), was added with stirring to 16 ml. of an aqueous solution containing 130 mg. of A47934 (pH 4.8, 0.1 mole) to give a final pH of 7.1. The solution was freeze-dried to yield 154 mg. of the A47934 monopotassium salt (K=2.14%).

EXAMPLE 9

Preparation of the Dipotassium Salt of A47934

Potassium hydroxide solution, 1.12 ml. (10 mg./ml., 0.1 mole), was added with stirring to 16 ml. of an aqueous solution containing 130 mg. of A47934 (0.1 mole, pH 4.8) to give a pH of 7.95. The solution was freeze-dried to yield 158 mg. of the dipotassium salt of A47934 (K=3.94%).

EXAMPLE 10

Preparation of the Barium Salt of A47934

Two ml. of a saturated solution of barium chloride was added to 4 ml. of an aqueous solution containing 100 mg. of A47934 to precipitate out the barium salt of A47934. The precipitate was centrifuged off, washed twice with 5 ml. portions of water and recentrifuged each time. The precipitate was resuspended in 10 ml.

water and freeze-dried to yield 76 mg. of the water-insoluble barium salt.

EXAMPLE 11

Preparation of the Calcium Salt of A47934

Two ml. of a saturated aqueous solution of calcium chloride was added with stirring to 4 ml. of an aqueous solution containing 100 mg. of A47934 to form a precipitate of the calcium salt of A47934. The precipitate was washed twice with 5-ml. portions of water, centrifuging each time, and the washed precipitate was suspended in 10 ml. water and freeze-dried. A yield of 87 mg. of the calcium salt of A47934 was obtained.

We claim:

1. A method of producing the A47934 antibiotic which comrpises cultivating *Streptomyces toyocaensis* NRRL 15009, or an A47934-producing variant or mutant thereof, in a culture medium containing assimilable sources of carbon, nitrogen, and inorganic saslts under submerged aerobic fermentation conditions until antibiotic activity is produced by said organism in said culture medium.

2. The method of claim 1 which includes the additional step of separating the A47934 antibiotic from the culture medium.

3. The method of claim 1 wherein the organism is *Streptomyces toyocaensis* NRRL 15009.

4. The method of claim 3 which includes the additional step of separating the A47934 antibiotics from the culture medium.

5. The biologically pure culture of *Streptomyces toyocaensis* NRRL 15009.

* * * * *